United States Patent
Webber et al.

(10) Patent No.: US 10,111,730 B2
(45) Date of Patent: Oct. 30, 2018

(54) ORTHODONTIC ALIGNER WITH ISOLATED SEGMENTS

(71) Applicant: Align Technology, Inc., San Jose, CA (US)

(72) Inventors: Peter Webber, Lafayette, CA (US); Jennifer C. Chen, Alhambra, CA (US); Yan Chen, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 322 days.

(21) Appl. No.: 14/539,725

(22) Filed: Nov. 12, 2014

(65) Prior Publication Data

US 2016/0128803 A1    May 12, 2016

(51) Int. Cl.
| | |
|---|---|
| *A61C 3/00* | (2006.01) |
| *A61C 7/08* | (2006.01) |
| *A61C 7/36* | (2006.01) |
| *A61C 7/00* | (2006.01) |

(52) U.S. Cl.
CPC ............... *A61C 7/08* (2013.01); *A61C 7/002* (2013.01); *A61C 7/36* (2013.01)

(58) Field of Classification Search
CPC .............. A61C 7/08; A61C 7/002; A61C 7/36
USPC .................................. 433/6, 18, 24
See application file for complete search history.

(56) References Cited

U.S. PATENT DOCUMENTS

| | | | |
|---|---|---|---|
| 6,572,372 B1 | 6/2003 | Phan et al. | |
| 7,192,273 B2 | 3/2007 | McSurdy, Jr. | |
| 2002/0192617 A1* | 12/2002 | Phan | A61C 7/00 433/6 |
| 2003/0190575 A1 | 10/2003 | Hilliard | |
| 2003/0207224 A1 | 11/2003 | Lotte | |
| 2004/0013993 A1* | 1/2004 | Ito | A61C 7/08 433/6 |
| 2008/0299508 A1* | 12/2008 | White | A61C 7/00 433/18 |
| 2009/0036889 A1* | 2/2009 | Callender | A61F 5/566 606/55 |
| 2009/0068612 A1* | 3/2009 | Wahab | A61C 7/08 433/24 |
| 2010/0075268 A1 | 3/2010 | Duran Von Arx | |
| 2011/0185525 A1 | 8/2011 | Stapelbroek | |
| 2014/0013993 A1 | 1/2014 | Donnelly | |

(Continued)

FOREIGN PATENT DOCUMENTS

| | | |
|---|---|---|
| KR | 200465679 Y1 | 3/2013 |
| WO | 03/084422 A2 | 10/2003 |

OTHER PUBLICATIONS

International Search Report and Written Opinion of hte International Searching Authority for PCT Application No. PCT/IB2015/002136 dated Feb. 22, 2016.

(Continued)

*Primary Examiner* — Nicholas Lucchesi
(74) *Attorney, Agent, or Firm* — Lowenstein Sandler LLP

(57) ABSTRACT

A segmented orthodontic aligner includes at least a first segment and a second segment. Each segment is shaped to fit over a set of teeth of a patient. The segmented aligner further includes a connector that joins the first segment to the second segment. The connector isolates the transmission of force between the first segment and the second segment.

16 Claims, 10 Drawing Sheets

(56) References Cited

U.S. PATENT DOCUMENTS

| | | | |
|---|---|---|---|
| 2015/0157421 A1* | 6/2015 | Martz | A61C 7/08 |
| | | | 433/6 |
| 2015/0216627 A1 | 8/2015 | Kopelman | |
| 2015/0257856 A1* | 9/2015 | Martz | A61C 7/14 |
| | | | 433/6 |
| 2015/0265376 A1 | 9/2015 | Kopelman | |
| 2015/0366637 A1 | 12/2015 | Kopelman et al. | |
| 2016/0081769 A1* | 3/2016 | Kimura | A61C 7/10 |
| | | | 433/6 |
| 2016/0128803 A1* | 5/2016 | Webber | A61C 7/08 |
| | | | 433/6 |
| 2017/0007365 A1* | 1/2017 | Kopelman | A61C 7/08 |
| 2017/0056236 A1* | 3/2017 | Yousefian | A61F 5/566 |
| 2017/0367791 A1* | 12/2017 | Raby | A61C 7/002 |

OTHER PUBLICATIONS

Carriere system—Carriere Motion, 1 page, 2014, Ortho Organizers Inc., downloaded from http://www.carrieresystem.com/distalizer.php only May 3, 2016.

\* cited by examiner

ORTHODONTIC ALIGNER WITH ISOLATED SEGMENTS

TECHNICAL FIELD

Embodiments of the present invention relate to the field of orthodontics and, in particular, to plastic orthodontic aligners.

BACKGROUND

Orthodontic procedures typically involve repositioning a patient's teeth to a desired arrangement in order to correct malocclusions and/or improve aesthetics. To achieve these objectives, orthodontic appliances such as braces, retainers, plastic aligners (also referred to as shell aligners), and the like can be applied to the patient's teeth by an orthodontic practitioner. The appliance is configured to exert force on one or more teeth in order to effect desired tooth movements. The application of force can be periodically adjusted by the practitioner (e.g., by altering the appliance or using different types of appliances) in order to incrementally reposition the teeth to a desired arrangement.

BRIEF DESCRIPTION OF THE DRAWINGS

The present invention is illustrated by way of example, and not by way of limitation, in the figures of the accompanying drawings.

DETAILED DESCRIPTION

Figure 1:
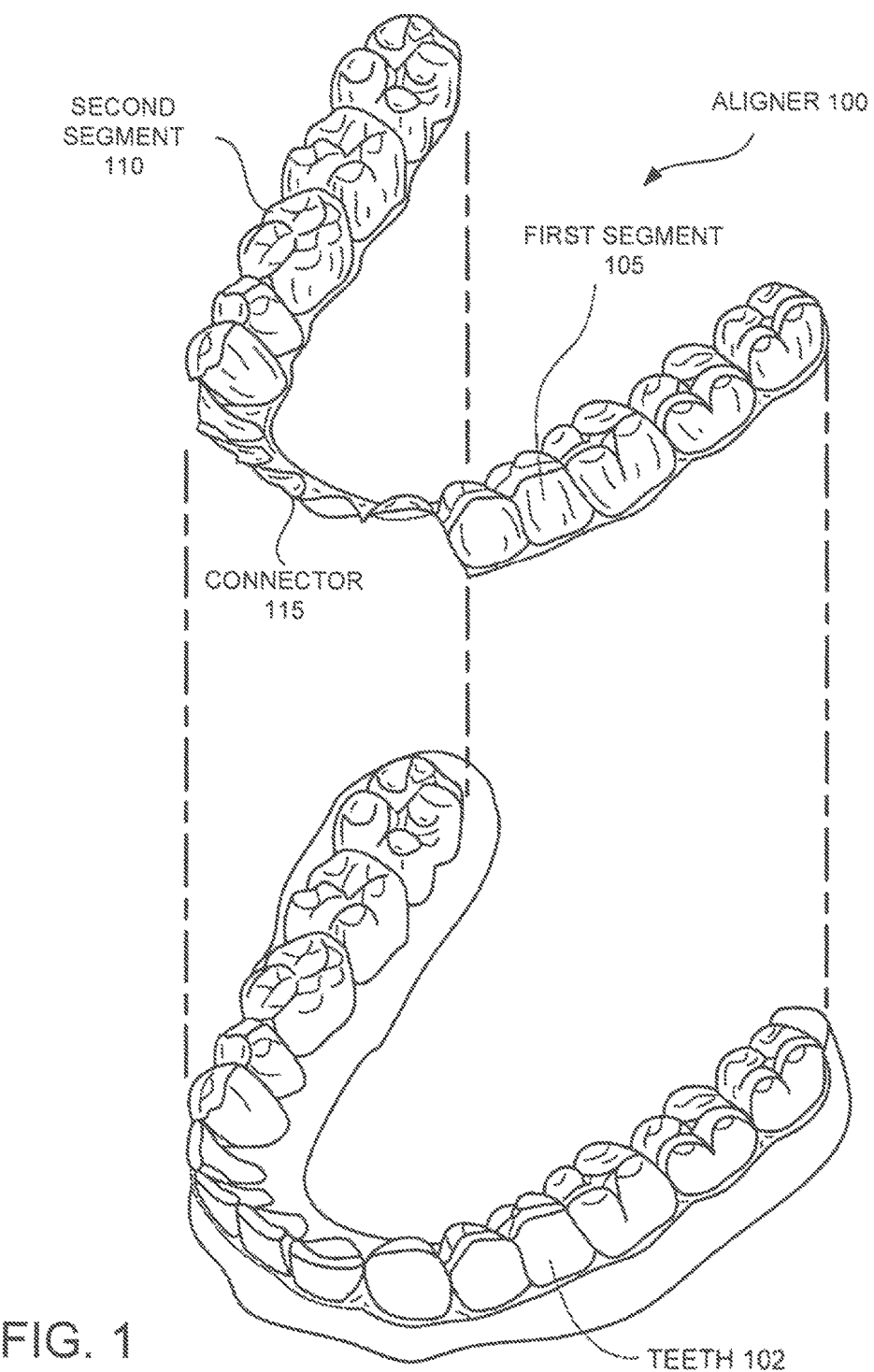
FIG. 1 illustrates a segmented plastic orthodontic aligner, in accordance with one embodiment.

In some instances, it may be desirable to isolate the forces applied to different groups of teeth. Current plastic aligners may not be able to effectively isolate the forces between different sets of teeth (e.g., between anterior teeth and posterior teeth). Described herein are embodiments of orthodontic aligners having segments joined by connectors that isolate forces between the segments (e.g., that isolate segments so that no forces or only minimal forces are applied between segments) and methods of manufacturing and using such orthodontic aligners. Force transmission between segments may be reduced compared to force transmission between different portions of a non-segmented orthodontic aligner. The segments and connectors can be individually fabricated and provided as discrete components, or separated from a larger aligner, as described below. The orthodontic aligners described herein, along with related systems and methods, can be employed as part of an orthodontic treatment procedure in order to reposition one or more teeth, maintain a current position of one or more teeth, or suitable combinations thereof. An orthodontic aligner can include multiple discrete shell segments, each including cavities shaped to receive at least portions of a patient's teeth that are joined by an elastic, rigid or semi-rigid connector to form a single appliance shell. The geometry, configuration, and material properties of the shell segments and/or connector can be selected to minimize or eliminate the transfer of forces between the segments. For example, the connector may be designed to prevent a clinically significant force from being applied to one or more teeth by a segment that does not cover those teeth. A clinically significant force is a force sufficient to change a position or alignment of a tooth. This enables separate and distinct forces to be applied to the teeth covered by each of the segments without interference or counter forces from other segments. Additionally, the segmented aligners disclosed herein may in some instances accommodate larger tooth movements than conventional unsegmented aligners, thus reducing the number of different aligners used to complete a course of orthodontic treatment. In some instances, force transmission may be minimized or eliminated in some directions without being affected in other directions. For example, distal or mesial forces may be minimized without reducing other forces between segments.

In some instances, a stiffness of the discrete shell segments is greater than a stiffness of the connector. This enables isolated force systems to be created, and enables the treatment of one or more particular teeth without reaction forces on other teeth. The segmented aligners joined by the force isolating connectors may improve the treatment of certain malocclusions in which separate force treatments to separate groups of teeth are preferred.

Shell segments may vary in design. In some instances, one or more of the discrete shell segments forming an aligner may be configured to receive only a single tooth. In some embodiments, one or more of the discrete shell segments may be configured to span or receive multiple teeth. An aligner may include segments of the same or different types with respect to a number of teeth spanned or received by the segment. For example, an appliance may include some discrete shell segment(s) that span or receive a single tooth, and some discrete shell segment(s) that span or receive multiple teeth. Connectors having varied shapes, material compositions and design may be used. The same type or a different type of connector may be used between each pair of adjacent segments.

An aligner as described herein may be included in a series of aligners so as to provide an orthodontic system for positioning teeth. Such an orthodontic system can include a sequence of orthodontic aligners each including a shell having a one or more cavities shaped to receive at least portions of teeth. The aligners may be successively worn by a patient to move one or more teeth from a first arrangement to a second arrangement. One or more of the aligners may be segmented and include connectors joining segments, as described herein.

Turning now to the drawings, FIG. 1 illustrates an example tooth repositioning appliance or orthodontic aligner 100 that can be worn by a patient in order to achieve an incremental repositioning of individual teeth 102 in the jaw. The orthodontic aligner 100 can include a shell (e.g., a continuous translucent polymeric shell or a segmented shell) having teeth-receiving cavities that receive and resiliently reposition the teeth 102. The orthodontic aligner 100 or portion(s) thereof may be indirectly fabricated using a physical model or mold of the teeth 102. For example, an aligner can be formed using a physical model of teeth 102 and a sheet of suitable layers of polymeric material. In some instances, an aligner 100 is directly fabricated, e.g., using rapid prototyping fabrication techniques, from a digital model of an aligner. An aligner 100 can fit over all teeth 102 present in an upper or lower jaw, or less than all of the teeth 102. The aligner 100 can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the aligner 100 can be a generic aligner configured to receive the teeth, but not necessarily shaped to match the topography of the patient's teeth.

In some cases, only certain teeth received by an aligner will be repositioned by the aligner while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the aligner as it is worn by the patient. Typically, no wires or other means will be provided for holding an aligner in place over the teeth. In some cases, however, it may be desirable to provide individual attachments or other anchoring elements (not shown) on teeth 102 with corresponding receptacles or apertures (not shown) in the orthodontic aligner 100 so that the aligner can apply a selected force on the tooth.

As shown, the orthodontic aligner 100 includes a first segment 105 and a second segment 110 separated by a connector 115. In the illustrated example, the first segment 105, second segment 110 and connector 115 are all portions of a single contiguous plastic body or shell. There may be a gap or space between the first segment 105 and the second segment 110, and the gap may be maintained by the connector 115. However, the portion of the aligner 100 that constitutes the connector 115 may have a lower rigidity and/or greater flexibility than the first segment 105 and the second segment 110. Alternatively, or additionally, the geometry of the connector 115 may be configured so as to have no or little contact with particular portions of one or more teeth. For example, the connector 115 may not contact the labial side of the anterior teeth (which the connector 115 may span). The lower rigidity, higher flexibility and/or geometric configuration is a result of the aligner 100 having been cut to remove a portion of the aligner 100 that would have covered a buccal region of the anterior teeth of a patient. The decreased rigidity, greater flexibility and/or geometric configuration of the aligner 100 at the connector 115 serves to isolate, reduce or eliminate force transmission between the first segment 105 and the second segment 110.

For example, since the aligner has been cut so as not to cover the buccal region of the anterior teeth, no lingual forces may be applied to those anterior teeth. This may ensure that no distal forces are applied to the anterior teeth, even if the posterior teeth covered by the first segment 105 and second segment 110 are exposed to forces for distalization.

As non-limiting examples, illustrated segments 105, 110 each receive multiple teeth. However, in some instances a segment may be configured to receive only a single tooth. In additional embodiments, an orthodontic aligner can include segments spanning a single tooth, segments spanning multiple teeth, as well as various combinations thereof. In aligner construction, segments that span a single tooth, as well as those that span multiple teeth, are not limited to any particular location within the arch, but can have a location selected in appliance design.

The connector 115 can be permanently affixed to the shell segments 105, 110 so that the shell segments 105, 110 cannot be nondestructively detached from each other. Alternatively, the connector 115 may be removable from the shell segments 105, 110. In one embodiment, the connector 115 serves the function of preventing a choking hazard that might be caused by the segments when separated.

Figure 2:
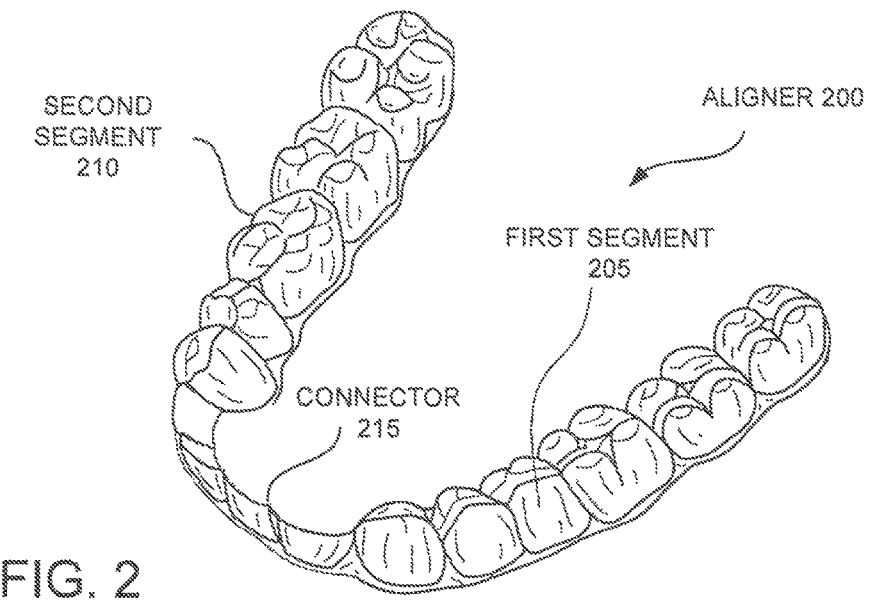
FIG. 2 illustrates a segmented plastic orthodontic aligner, in accordance with another embodiment.

FIG. 2 illustrates a segmented plastic orthodontic aligner 200, in accordance with another embodiment. Similar to aligner 100, aligner 200 includes a first segment and a second segment 210 joined by a connector 215. As with aligner 100, the connector 215 in aligner 200 is formed by cutting away a portion of the body of the aligner 200. However, in aligner 200 a portion of the aligner that would contact the lingual or palatal region of a patient's anterior teeth is cut out. Thus, the transfer of buccal forces to the anterior teeth may be avoided. Such forces may be avoided for the anterior teeth even in instances where forces are applied to posterior teeth.

Figure 3:
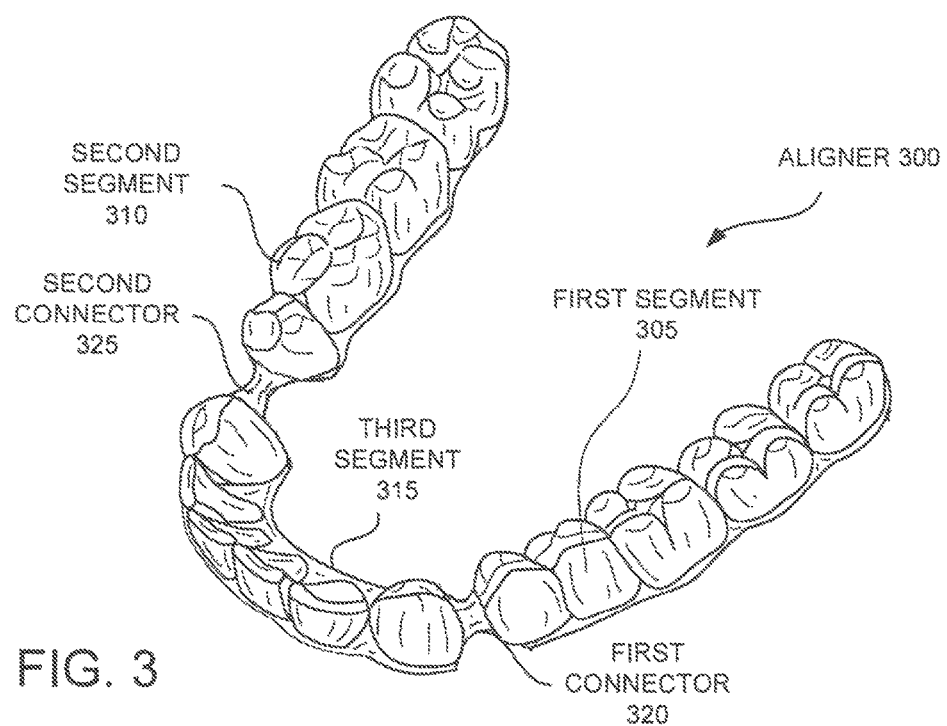
FIG. 3 illustrates a segmented plastic orthodontic aligner, in accordance with another embodiment.

FIG. 3 illustrates a segmented plastic orthodontic aligner 300, in accordance with another embodiment. The aligner 300 includes a first segment 305, a second segment 310 and a third segment 315. The first segment 305 and third segment 315 are joined by a first connector 320. Similarly, the second segment 310 and third segment 315 are joined by a second connector 325. The first connector 320 and second connector 325 may be an elastomer (e.g., an elastomer adhesive), semi-rigid materials including thermoset and thermoplastic materials, a semi-rigid metal connector, and so on. In one embodiment, the first connector 320 and second connector 325 are an elastomer with a shore hardness of A20 to A80 and an elastic modulus of about 100 pounds per square inch (psi) to about 100,000 psi. In one embodiment, the first connector 320 and second connector 325 are semi-rigid thermoset or thermoplastic materials with a shore hardness from D30 to D80 and an elastic modulus of about 100,000 psi to about 350,000 psi. In one embodiment, the first connector 320 and second connector 325 are made of metal (e.g., metal wire, metal ribbon, etc.). In one embodiment, the connectors 320, 325 are formed from an elastic adhesive (e.g., an elastomer adhesive) that effectively bonds the segments with an elastic bond. In another embodiment, the connectors 320, 325 are formed from a polyurethane elastomer (PTE). In another embodiment, connectors 320, 325 are formed from plastics, metals (e.g., arch wires), and/or other materials. The connectors 320, 325 may be elastic, totally rigid, connected with a pivot, and/or connected with a geometry that transmits certain directional forces without transmitting other forces.

Connectors 320, 325 may be formed from a single material or from multiple materials. The materials may be arranged in one or more layers. For example, layers of different materials or layers of the same material may be used to form the connectors 320, 325. Properties of the material used to form the connectors 320, 325 such as resiliency, elasticity, hardness/softness, color, and the like can be determined, at least partially, based on the selected material, material shape, material dimensions, layers of material, and/or material thickness. In one embodiment, the connectors 320, 325 are formed from elastic materials such as an elastomer material.

In some instances, the connectors 320, 325 can be configured such that one or more properties are uniform along a length or portion of connectors. Additionally, one or more properties of the connectors may vary along a length or portion of the connectors. For example, a connector 320, 325 may have substantially uniform thickness along a length or portion, or may vary along a length or portion. As will be appreciated, characteristics of the connector may be selected so as to reduce or eliminate force transfer between different segments of the aligner and/or groups of teeth.

In the illustrated example aligner 300, the connectors 320, 325 operate to reduce or eliminate force transmission between left and right posterior teeth and anterior teeth of a patient. This enables the posterior teeth to be distalized as a unit, while separate movement can be applied to the anterior teeth (e.g., to the patient's incisors). Alternatively, a mesial force may be applied to the posterior teeth without exerting a mesial force on the anterior teeth. The treatments of the posterior teeth would not affect or interfere with the treatments of the posterior teeth. Likewise, the treatments of the posterior teeth would not affect or interfere with the treatments of the anterior teeth.

Figure 4:
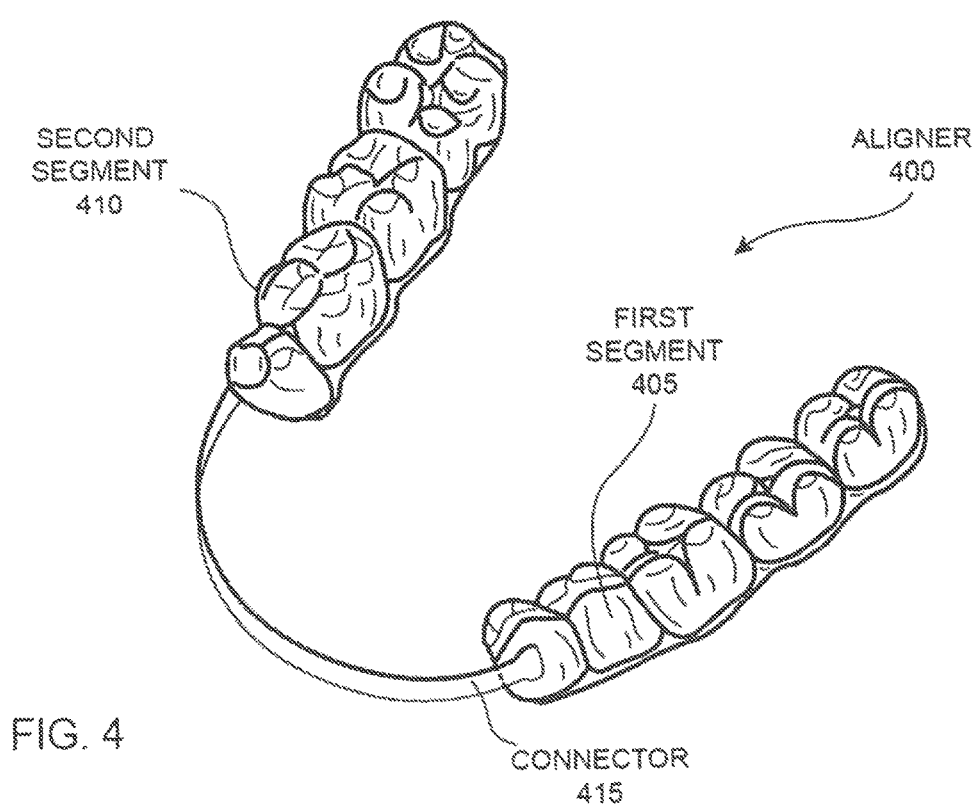
FIG. 4 illustrates a segmented plastic orthodontic aligner, in accordance with another embodiment.

FIG. 4 illustrates a segmented plastic orthodontic aligner 400, in accordance with another embodiment. The aligner 400 includes a first segment 405 joined to a second segment 410 by a bridge-like connector 415. The connector 415 is a semi-rigid material that flexes rather than transferring forces between the first and second segments 405, 410. The connector 415 may be a pre-formed connector, which may be glued or mechanically attached to the segments.

In one embodiment, the segments 405, 410 each include a retention feature that is sized and shaped to retain an end of the connector 415. For example, the connector 415 may snap into place in the features. These features may be designed into the aligner 400. For example, these features may be included in mold that is used to form the aligner so that the aligner includes the features. Alternatively, these features may be formed in (e.g., cut into) the segments and/or attached to the segments after the segments are formed. Some examples of retention features include grooves, ridges, protrusions, indentations, male or female portions of mechanical snaps or locks, etc. The retention features can be used to prevent the accidental displacement or release of the connector 415 from a desired position, thereby ensuring that the aligner 400 does not separate or pose a choking hazard.

Figure 5:
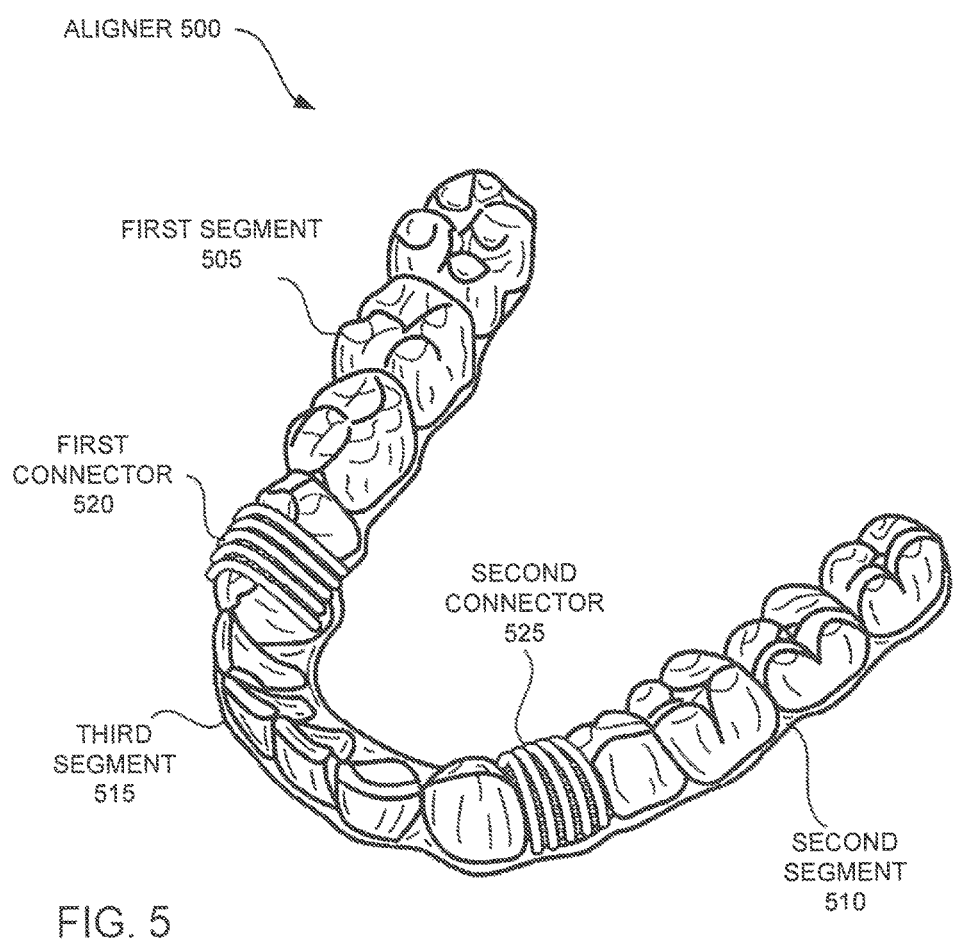
FIG. 5 illustrates a plastic orthodontic aligner, in accordance with another embodiment.

FIG. 5 illustrates a plastic orthodontic aligner 500, in accordance with another embodiment. The aligner 500 includes a first segment 505 joined to a first side of a third segment 515 by a first connector 520. The aligner 500 additionally includes a second segment 510 joined to a second side of the third segment 515 by a second connector 525. The first and second connectors 520, 525 are corrugated connectors with an accordion-like shape. The corrugated configuration will flex before applying clinically significant forces between segments. Thus, the corrugation between segments reduces force transmitted between segments during treatment. In one embodiment, the corrugated connectors 520, 525 are formed of the same material as the segments 505-515 (e.g., an elastomer). In one embodiment, as shown, the connectors 520, 525 and the segments 505-515 form a single contiguous shell body. Alternatively, the connectors 520, 525 may be separate components that are attached to the segments 505-515. In such an instance, the connectors 520-525 may be the same material as the segments or a different material. For example, the connectors 520-525 may be formed of an elastomer.

Figure 6:
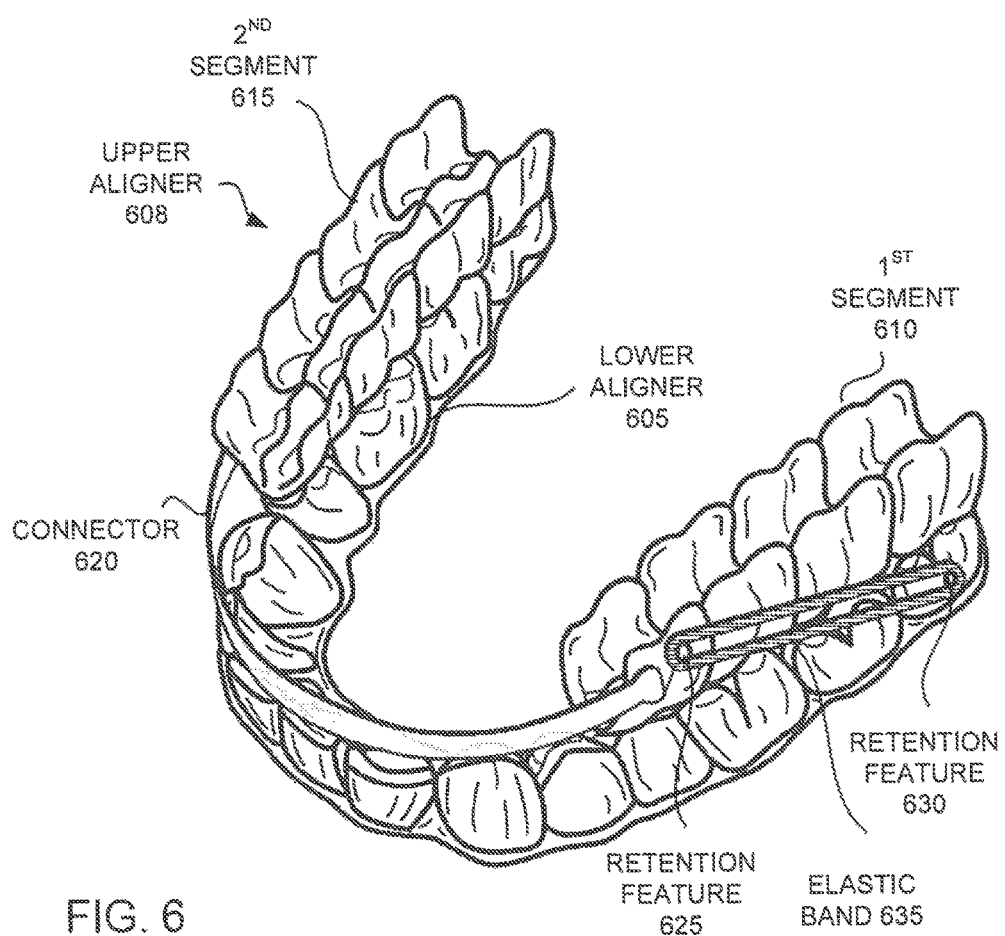
FIG. 6 illustrates a pair of plastic orthodontic aligners designed to apply forces to upper posterior teeth without applying forces to upper anterior teeth, in accordance with another embodiment.

FIG. 6 illustrates a pair of plastic orthodontic aligners designed to apply forces to upper posterior teeth without applying forces to upper anterior teeth, in accordance with another embodiment. The pair of aligners includes an upper aligner 608 and a lower aligner 605. The lower aligner 605 is a conventional unsegmented aligner that includes a retention feature 630. As shown, the retention feature 630 may be located at a molar or other posterior tooth. The retention feature may be a slit, cut, groove, protrusion, or other feature that may secure one end of an elastic band 635 (e.g., such as a rubber band). Alternatively, the lower aligner 605 may include a discontinuity such as a cut, flap, aperture (e.g., opening, window, gap, notch, etc.) rather than a retention feature. A retention feature may accordingly be bonded directly to a patient's tooth at the location of the discontinuity. The discontinuity may expose the retention feature when the lower aligner 605 is worn by the patient.

The upper aligner 605 is a segmented aligner including a first segment 610 and a second segment 615 joined by a connector 620. The first segment 610 includes a retention feature 625 that is to secure a second end of the elastic band 635. As shown, the retention feature 625 may be located at a canine or other anterior tooth. Alternatively, the first segment 610 may include a discontinuity such as a cut, flap, aperture (e.g., opening, window, gap, notch, etc.) rather than a retention feature. A retention feature may accordingly be bonded directly to a patient's tooth at the location of the discontinuity. The discontinuity may expose the retention feature when the upper aligner 608 is worn by the patient.

The elastic band 635 may apply a distal force to the first segment, and thus to a group of teeth covered by the first segment 610. A similar elastic band may extend between additional retention features on the second segment 615 and the lower aligner 605, and may apply a distal force to the second segment and thus to a group of teeth covered by the second segment 615. The connector 620 may isolate forces so that no forces are applied to any upper anterior teeth of the patient. In an alternative embodiment, the retention feature 625 may be located on an upper posterior tooth, and the retention feature 630 may be located on a lower anterior tooth. In such a configuration a mesial force may be applied to the second segment 615 without being applied to the first segment 610.

In an alternative example, the upper and/or lower aligner may be any of the segmented aligners described herein. For example, the upper aligner may be similar to aligner 300 of FIG. 3, and may include three segments joined by two connectors rather than two segments joined by a single connector.

The appliances described herein can be used in combination with one or more attachments mounted onto one or more of the received teeth. Accordingly, the topography of the shell segment can be modified to accommodate the attachment (e.g., with a suitable receptacle for receiving the attachment). The attachment can engage the shell segments and/or elastics to transmit repositioning forces to the underlying teeth, as previously described herein. Alternatively or in addition, the attachment can be used to retain the appliance on the patient's teeth and prevent it from inadvertently becoming dislodged. For example, teeth with no undercuts (e.g., central teeth, lateral teeth) may require an attachment to ensure correct engagement of the attachment onto the teeth, while teeth with natural undercuts (e.g., molars) may not require an attachment. The attachment can be mounted onto any suitable portion of the tooth, such as on a buccal or lingual surface of the tooth.

Figure 7:
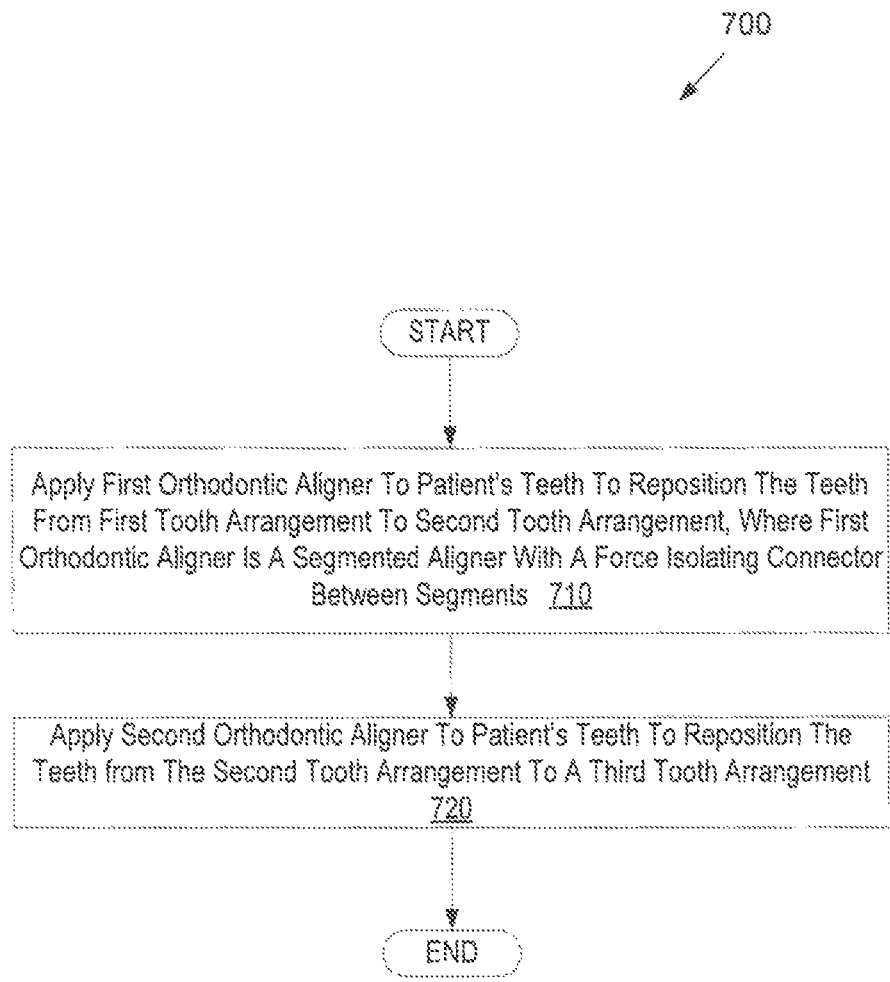
FIG. 7 illustrates a flow diagram of one embodiment for a method of orthodontic treatment using a sequence of aligners.

FIG. 7 illustrates a flow diagram of one embodiment for a method 700 of orthodontic treatment using a sequence of aligners. The method 700 can be practiced using any of the aligners or aligner sets described herein. In block 710, a first orthodontic aligner is applied to a patient's teeth in order to reposition the teeth from a first tooth arrangement toward a second tooth arrangement. The patient's teeth are arranged such that different forces are to be applied to teeth by different segments. These forces may have been incompatible using traditional aligners, because reactive forces from some segments may have acted to undermine forces to be applied to teeth by other segments.

At block 720, a second orthodontic aligner is applied to the patient's teeth in order to reposition the teeth from the second tooth arrangement to a third tooth arrangement. The repositioning of the teeth from the second arrangement to the third arrangement may be accomplished using traditional aligners (e.g., unsegmented aligners). Accordingly, a traditional unsegmented aligner may be used to reposition the teeth from the second arrangement to the third arrangement. Alternatively, the second orthodontic aligner may be another segmented aligner that isolates forces between different segments. The second orthodontic aligner may be segmented in the same manner as the first orthodontic aligner or in a different manner from the first orthodontic aligner. For example, the first orthodontic aligner may include two segments separated by a single connector, and the second orthodontic aligner may include three segments, each joined by a different connector. The different aligners may be segmented, for example, to apply forces to different groups of teeth.

The method 700 can be repeated using any suitable number and combination of sequential aligners in order to incrementally reposition the patient's teeth from an initial arrangement to a target arrangement. The aligners can be generated all at the same stage or in sets or batches (e.g., at the beginning of a stage of the treatment), and the patient can wear each aligner until the pressure of each aligner on the teeth can no longer be felt or until the maximum amount of expressed tooth movement for that given stage has been achieved. Multiple different aligners (e.g., a set) can be designed and even fabricated prior to the patient wearing any aligner. After wearing an aligner for an appropriate period of time, the patient can replace the current aligner with the next aligner in the series until no more aligners remain. The aligners are generally not affixed to the teeth and the patient may place and replace the aligners at any time during the procedure (e.g., patient-removable aligners).

The final aligner or several aligners in the series may have a geometry or geometries selected to overcorrect the tooth arrangement. For instance, one or more aligners may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an aligner with a geometry that is positioned beyond a desired intermediate or final position may shift the individual teeth toward the position at a greater rate). In such cases, the use of an aligner can be terminated before the teeth reach the positions defined by the aligner. Furthermore, over-correction may be deliberately applied in order to compensate for any inaccuracies or limitations of the aligner.

Figure 8:
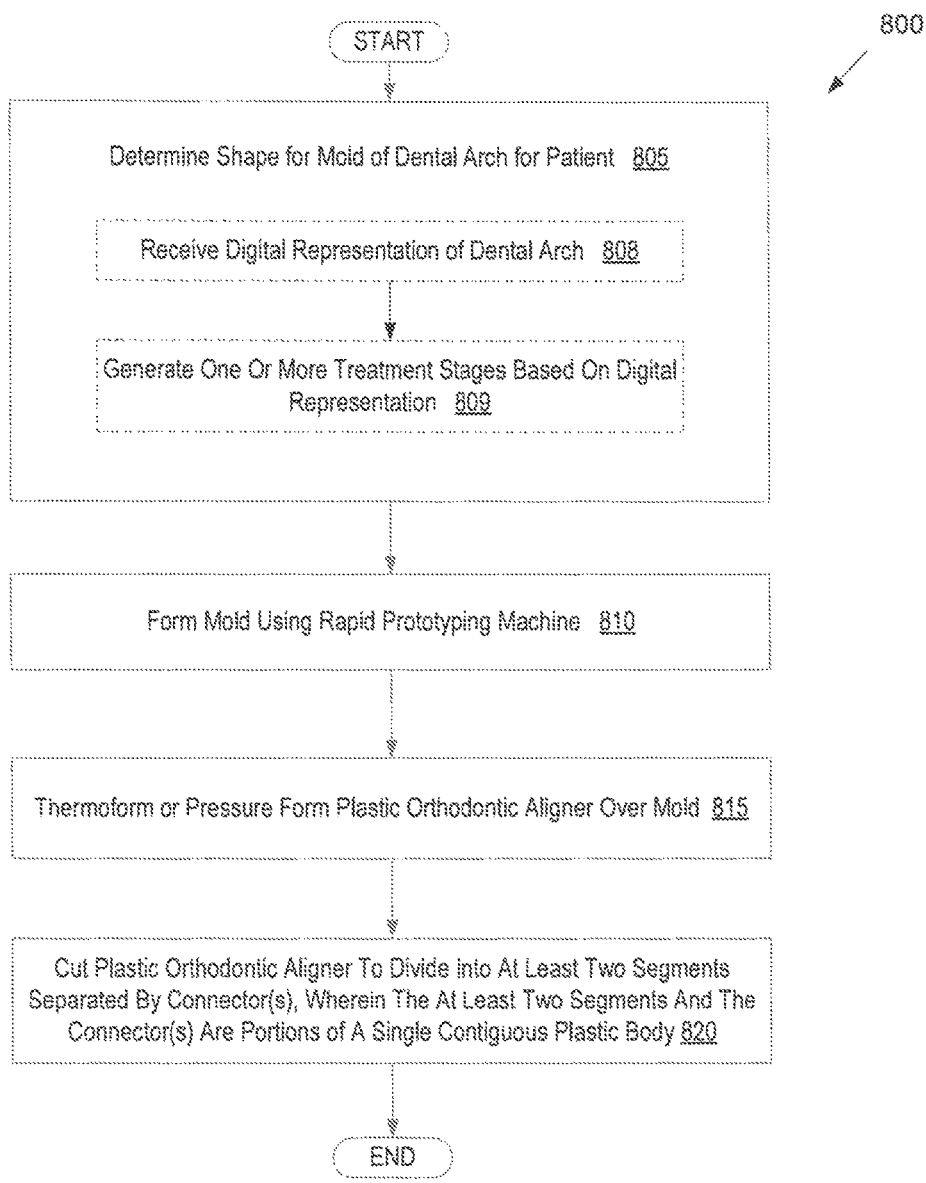
FIG. 8 illustrates a flow diagram of one embodiment for a method of manufacturing a segmented aligner having a connector that isolates force transmission between segments.

FIG. 8 illustrates a flow diagram of one embodiment for a method 800 of manufacturing a segmented aligner having a connector that isolates, reduces or eliminates force transmission between segments. In some embodiments, one or more operations of method 800 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 800 may be performed by a computing device such as computing device 1101 of FIG. 11. Additionally, some operations may be performed by a fabrication machine based on instructions received from processing logic. Some operations may alternately be performed by a user.

At block 805 of method 800, a shape is determined for a mold of a dental arch for a patient. The shape may be determined by digitally planning an intermediate or final target arrangement of the patient's teeth, and fabricating a mold of a dental arch that reflects that intermediate or final target arrangement. Alternatively, the shape may be determined by taking an impression of a patient's arch and generating a mold from the impression. Thus, the mold or model can be generated from dental impressions or scanning (e.g., of the patient's intraoral cavity, of a positive or negative model of the patient's intraoral cavity, or of a dental impression formed from the patient's intraoral cavity).

Aligner fabrication or design can make use of one or more physical or digital representations of the patient's teeth. Representations of the patient's teeth can include representations of the patient's teeth in a current arrangement, and may further include representations of the patient's teeth repositioned in one or more treatment stages. Treatment stages can include a desired or target arrangement of the patient's teeth, such as a desired final arrangement of teeth. Treatment stages can also include one or more intermediate arrangements of teeth (e.g., planned intermediate arrangements) representing arrangements of the patient's teeth as the teeth progress from a first arrangement (e.g., initial arrangement) toward a second or desired arrangement (e.g., desired final arrangement).

In one embodiment, at block 808 a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In one embodiment, at block 809 one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

At block 810, the mold is fabricated based on the determined shape. This may include using a three-dimensional virtual model of the dental arch and sending instructions to a rapid prototyping machine (e.g., a three-dimensional printer) to fabricate the mold. In one embodiment, the breakable mold is fabricated using a rapid prototyping manufacturing technique. One example of a rapid prototyping manufacturing technique is 3D printing. 3D printing includes any layer-based additive manufacturing processes. A 3D printer may receive an input of the 3D virtual model of the mold (e.g., as a computer aided drafting (CAD) file or 3D printable file such as a sterolithography (STL) file), and may use the 3D virtual model to create the mold. 3D printing may be achieved using an additive process, where successive layers of material are formed in proscribed shapes. 3D printing may be performed using extrusion deposition, granular materials binding, lamination, photopolymerization, or other techniques.

In one embodiment, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Each layer may have a thickness of between 25 microns and 200 microns. Once all of the layers of the mold are formed, the mold may be cleaned and cured.

At block 815, a plastic orthodontic aligner is formed over the mold. This may include sending instructions to a pressure forming or thermoforming machine to cause a sheet of material to be pressure formed or thermoformed over the mold to form a body of the aligner. The sheet may be, for example, a sheet of plastic (e.g., an elastic thermoplastic). To thermoform the shell or aligner over the mold, the sheet of material may be heated to a temperature at which the sheet becomes pliable. Pressure may concurrently be applied to the sheet to form the now pliable sheet around the breakable mold. Once the sheet cools, it will have a shape that conforms to the mold. In one embodiment, a release agent (e.g., a non-stick material) is applied to the mold before forming the aligner. This may facilitate later removal of the mold from the aligner. The plastic orthodontic aligner may include a first segment and a second segment that are formed together (e.g., that are formed simultaneously). In some embodiments, a connector may also be formed together with the formation of the first and second segments.

Other exemplary methods for fabricating aligners or discrete segments and/or connectors of aligners include rapid prototyping, stereolithography, or computer numerical control (CNC) milling. The material of the aligner or shell segments can be translucent, such as a translucent polymer.

At block 820, the plastic orthodontic aligner is cut to divide the aligner into at least two segments separated by connectors. This may include sending instructions to a cutting machine to cause the cutting machine to cut the aligner at specified coordinates. The cutting machine may be, for example, a laser cutter, plasma cutter or mill. The at least two segments and the connectors are portions of a single contiguous plastic body. The discrete shell segments each include one or more cavities shaped to receive at least portions of teeth. The shell segments can collectively receive a continuous span of teeth. The number and shape of the shell segments can be selected to accommodate the desired tooth movements, and the connectors can isolate forces to permit different tooth movements to different sets of teeth. The aligner may also be marked and/or trimmed along a gingival cut line.

A set of aligners can be fabricated, each shaped to accommodate a tooth arrangement specified by one of the treatment stages, such that the aligners can be sequentially worn by the patient to incrementally reposition the teeth from the initial arrangement to the target arrangement. The aligner set may include one or more of the segmented aligners described herein. The properties of the shell segments and connectors of such segmented aligners (e.g., number, geometry, configuration, material characteristics) can be selected to elicit the tooth movements specified by the corresponding treatment stage. At least some of these properties can be determined via suitable computer software or other digital-based approaches. The fabrication of the aligner may involve creating a digital model of the aligner to be used as input to a computer-controlled fabrication system.

Figure 9:
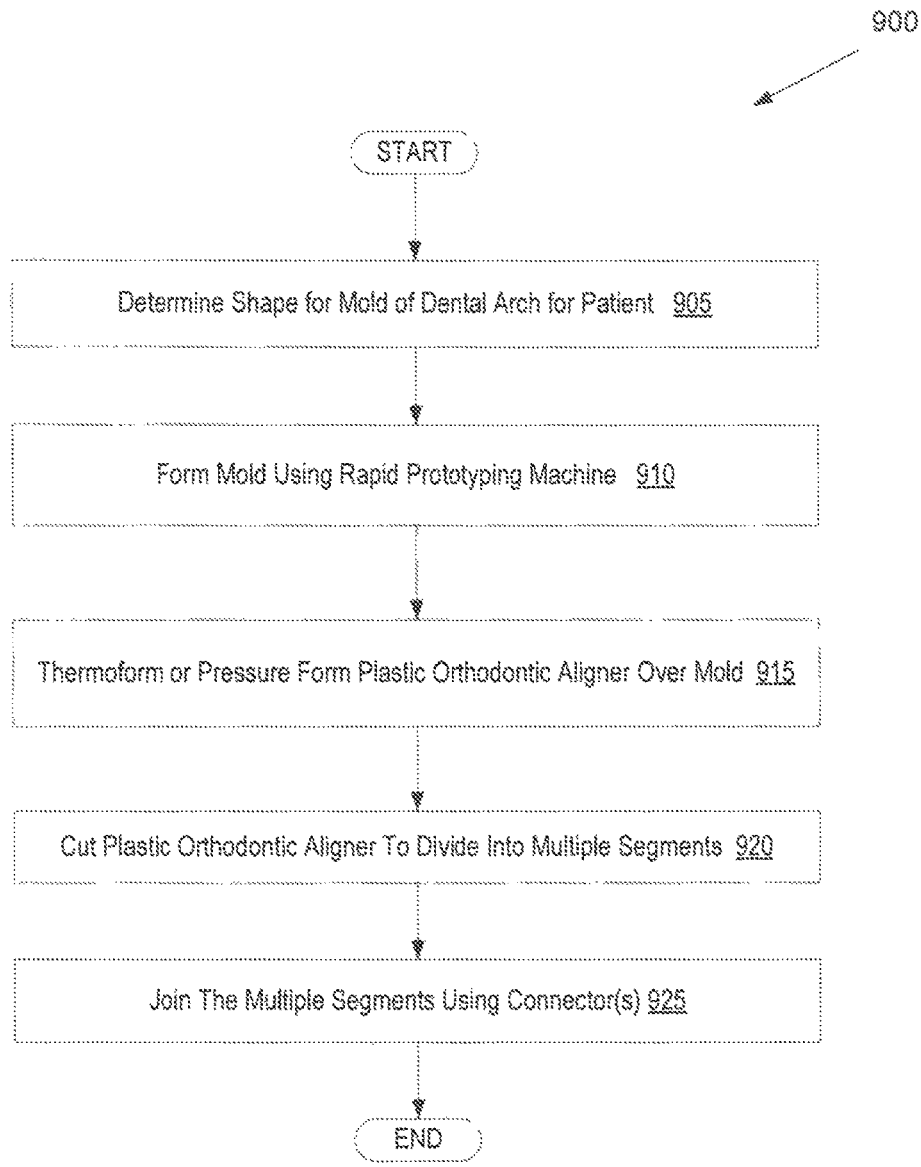
FIG. 9 illustrates a flow diagram of another embodiment for a method of manufacturing a segmented aligner having a connector that isolates force transmission between segments.

FIG. 9 illustrates a flow diagram of another embodiment for a method 900 of manufacturing a segmented aligner having a connector that isolates force transmission between segments. In some embodiments, one or more operations of method 900 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 900 may be performed by computing device such as computing device 1101 of FIG. 11. Additionally, some operations may be performed by a fabrication machine based on instructions received from processing logic. Some operations may alternately be performed by a user (e.g., based on user interaction with a mold modeling module or drafting program).

At block 905 of method 900, a shape is determined for a mold of a dental arch for a patient. The shape may be determined by digitally planning an intermediate or final target arrangement of the patient's teeth, and fabricating a mold of a dental arch that reflects that intermediate or final target arrangement. Alternatively, the shape may be determined by taking an impression of a patient's arch and generating a mold from the impression. At block 910, the mold is fabricated based on the determined shape (e.g., based on sending instructions to a rapid prototyping machine). This may include using a three-dimensional virtual model of the dental arch and a rapid prototyping machine (e.g., a three-dimensional printer) to fabricate the mold.

At block 915, a plastic orthodontic aligner is formed over the mold (e.g., based on sending instructions to a thermoforming or pressure forming machine). In one embodiment, the plastic orthodontic aligner is thermoformed or pressure formed over the mold. Other exemplary methods for fabricating aligners or discrete segments and/or connectors of aligners include rapid prototyping, stereolithography, or computer numerical control (CNC) milling. The material of the aligner or shell segments can be translucent, such as a translucent polymer. Alternatively, the material may have any other desired color or colors.

At block 920, the plastic orthodontic aligner is cut to divide the aligner into at least two segments separated by connectors (e.g., based on sending instructions to a cutting machine). The aligner may be cut using a laser cutter, a plasma cutter, a mill, or a mechanical cutter. The aligner is cut to separate the aligner into multiple discreet segments that are not joined.

At block 925, the discrete shell segments are joined using a connector (or multiple connectors), thereby forming a single aligner shell. In one embodiment, instructions are sent to a machine to cause the machine to join the segments to the connector. Alternatively, a prompt may be output to a display to instruct a user to manually connect the segments to the connector. The connector may be an elastic material. Alternatively, the connector may be a plastic such as a semi-rigid plastic. Other elastic or semi-rigid materials may also be used. In many embodiments, the connector is translucent. The connector can be provided as strips, bands, sheets, meshes, coatings, layers, tubes, elastic glues, or suitable combinations thereof, and can be fabricated from any suitable material. Example fabrication methods for elastics include extrusion, rapid prototyping, spraying, thermoforming, or suitable combinations thereof. The characteristics of the connector (e.g., length, width, thickness, area, shape, cross-section, stiffness, etc.) may be homogeneous throughout the bulk of the elastic material, or may be variable. For example, different portions of connector may have different thicknesses, thereby altering the local compliance of the aligner. Furthermore, in some instances, the connector can have anisotropic characteristics. As an example, the connector may be relatively compliant along a first direction, and less compliant (or noncompliant) along a second direction. The directionality of the connector's flexibility can be used to mitigate the transfer of forces between teeth while still providing structure and stability to the aligner.

The connector can be coupled to the segments using suitable adhesives or bonding agents. In some instances, the connector may have adhesive properties, thus enabling the connector to be directly coupled to the shell segments without the use of additional external agents. Example methods of attaching the connector to the shell segments include extrusion, spraying, coating, dipping, or suitable combinations thereof. The connector may also be physically connected to the segments using snaps, clasps, locks, etc. For example, the connector may include a male end of a snap and a retention feature in a segment may include a female end of the snap. In one embodiment, additional information may be sent to one or more machines to cause the machines to form a retention feature in a segment. The retention feature may be to retain an elastic band that may later be attached to the retention feature and to another retention feature on another aligner, segment of aligner or tooth. In one embodiment, forming the retention feature includes cutting a slit or groove in a segment of the aligner.

Figure 10:
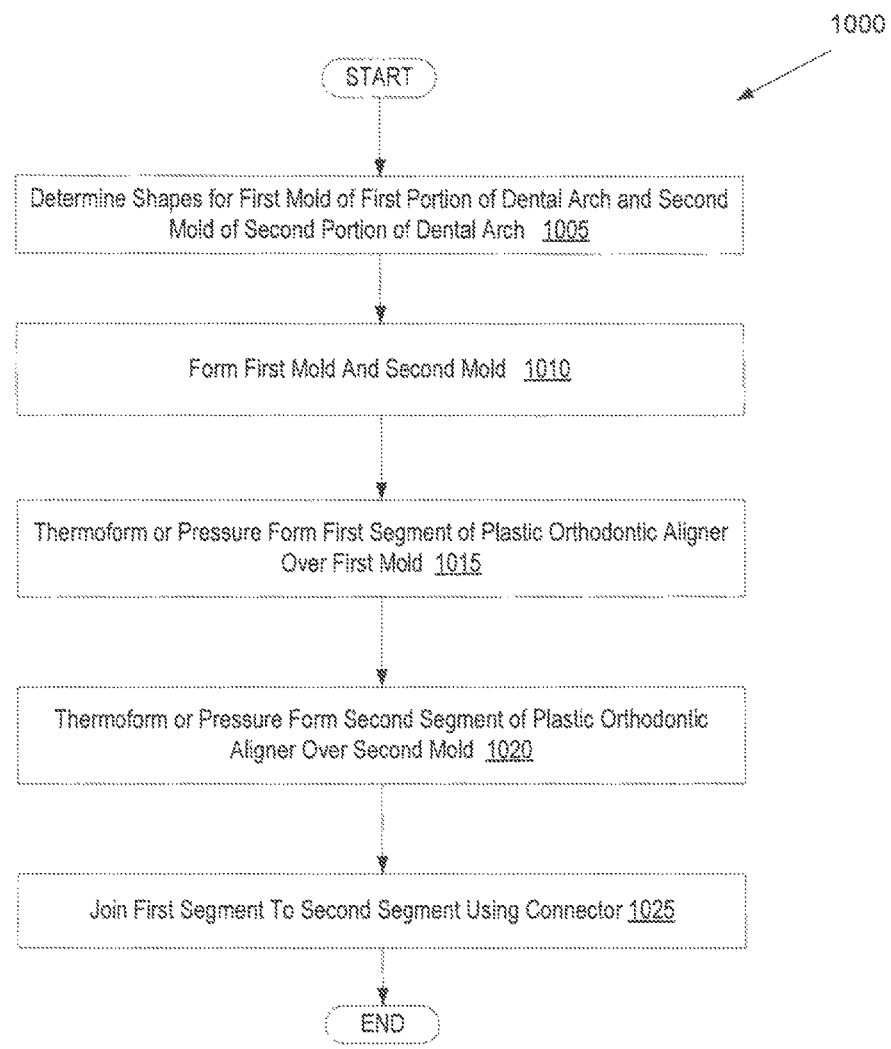
FIG. 10 illustrates a flow diagram of another embodiment for a method of manufacturing a segmented aligner having a connector that isolates force transmission between segments.

FIG. 10 illustrates a flow diagram of another embodiment for a method of manufacturing a segmented aligner having a connector that isolates, reduces or eliminates force transmission between segments. In some embodiments, one or more operations of method 1000 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1000 may be performed by computing device such as computing device 1101 of FIG. 11. Additionally, some operations may be performed by a fabrication machine based on instructions received from processing logic. Some operations may alternately be performed by a user (e.g., based on user interaction with a mold modeling module or drafting program).

At block 1005 of method 1000, a shape is determined for a first mold of a first dental arch and for a second mold of a second portion of the dental arch. The first mold may represent a first set of teeth of a patient and the second mold may represent a second set of teeth of the patient. The shapes may be determined by digitally planning an intermediate or final target arrangement of the patient's teeth. Alternatively, the shapes may be determined by taking impressions of a patient's arch. At block 1010, the molds are fabricated based on the determined shapes. This may include using a three-dimensional virtual model of the dental arch and a rapid prototyping machine (e.g., a three-dimensional printer) to fabricate the molds.

At block 1015, a first segment of a plastic orthodontic aligner is formed over the first mold. In one embodiment, the first segment of the plastic orthodontic aligner is thermoformed or pressure formed over the mold. At block 1020, a second segment of the plastic orthodontic aligner is formed over the second mold. Exemplary methods for fabricating the segments include thermoforming, rapid prototyping, stereolithography, or computer numerical control (CNC) milling.

At block 1025, the discrete shell segments are joined using a connector (or multiple connectors), thereby forming a single aligner shell. The connector may be an elastic material. Alternatively, the connector may be a plastic such as a semi-rigid plastic. Other elastic or semi-rigid materials may also be used.

Figure 11:
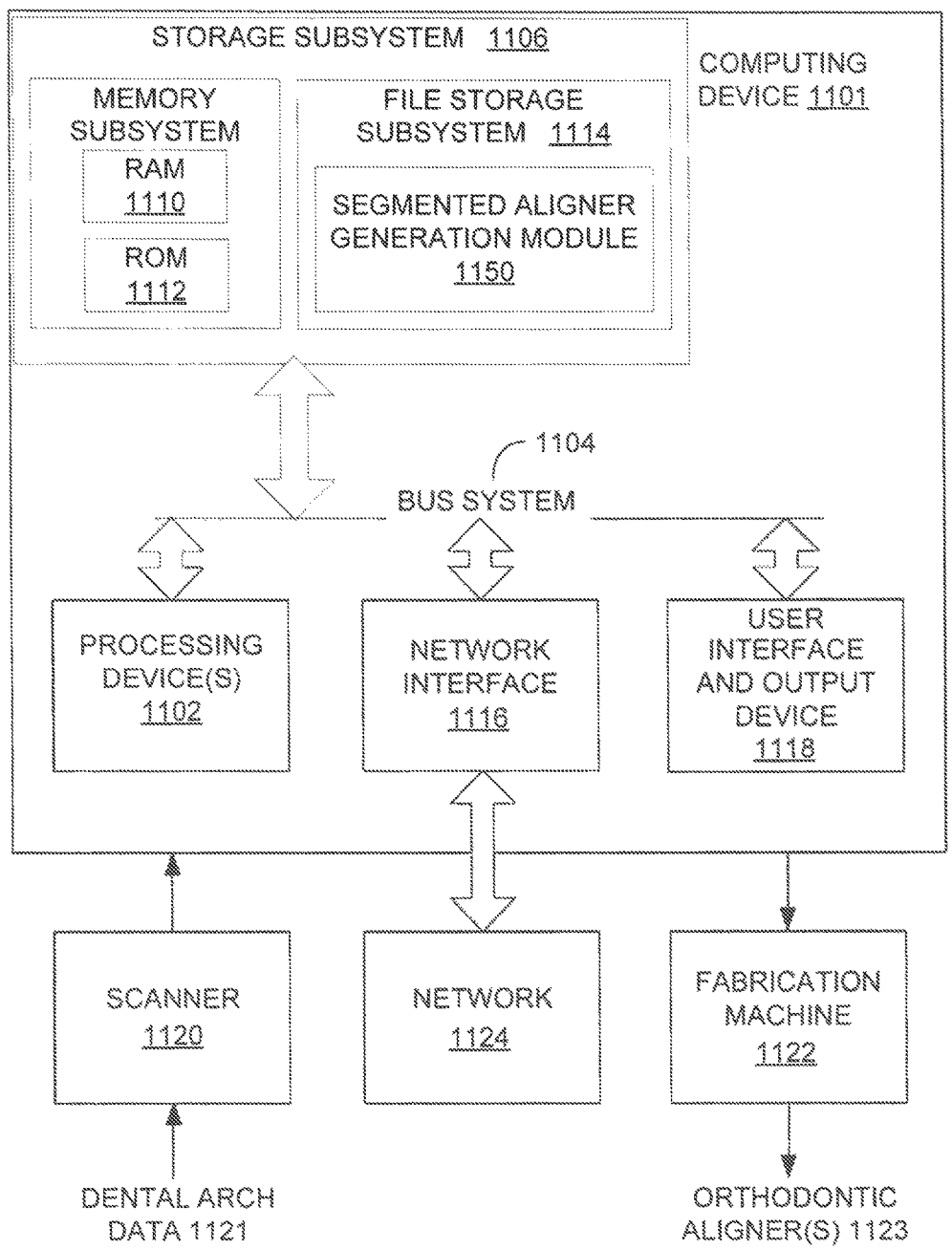
FIG. 11 illustrates a block diagram of an example computing device, in accordance with embodiments of the present invention.

FIG. 11 is a simplified block diagram of a system 1100 that may be used in executing methods and processes described herein. The system 1100 typically includes a computing device 1101 connected to a network 1124, a scanner 1120 and/or a fabrication machine 1122. The computing device 1101 may be connected (e.g., networked) to other machines in a Local Area Network (LAN), an intranet, an extranet, or the Internet. For example, the computing device 1101 may be networked fabrication machine 1122, which may be a rapid prototyping apparatus such as a 3D printer or SLA apparatus. The computing device 1101 may operate in the capacity of a server or a client machine in a client-server network environment, or as a peer machine in a peer-to-peer (or distributed) network environment. The computing device 1101 may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term computing device shall also be taken to include any collection of machines (e.g., computers) that individually or jointly execute a set (or multiple sets) of instructions to perform any one or more of the methodologies discussed herein.

Computing device 1101 includes at least one processing device 1102 that communicates with one or more peripheral devices via bus subsystem 1104. Processing device 1102 represents one or more general-purpose processors such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1102 may also be one or more special-purpose processing devices such as an application specific integrated circuit (ASIC), a field programmable gate array (FPGA), a digital signal processor (DSP), network processor, or the like. Processing device 1102 is configured to execute the processing logic (instructions) for performing operations and steps discussed herein.

Peripheral devices typically connected to processing device 1102 include a storage subsystem 1106 (memory subsystem 1108 and file storage subsystem 1114), a set of user interface input and output devices 1118, and an interface to outside networks 1116. This interface is shown schematically as "Network Interface" block 1116, and is coupled to corresponding interface devices in other data processing systems via communication network interface 1124.

The user interface input devices 1118 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1106 maintains basic programming of the computing device 1101, including computer readable media having instructions (e.g., operating instructions, etc.), and data constructs. The program modules discussed herein are typically stored in storage subsystem 1106. Storage subsystem 1106 typically includes memory subsystem 1108 and file storage subsystem 1114. Memory subsystem 1108 typically includes a number of memories (e.g., RAM 1110, ROM 1112, etc.) including computer readable memory for storage of fixed instructions, instructions and data during program execution, basic input/output system, etc. File storage subsystem 1114 provides persistent (non-volatile) storage for program and data files, and can include one or more removable or fixed drives or media, hard disk, floppy disk, CD-ROM, DVD, optical drives, and the like.

The file storage subsystem 1114 may include a machine-readable storage medium (or more specifically a non-transitory computer-readable storage medium) on which is stored one or more sets of instructions embodying any one or more of the methodologies or functions described herein. A non-transitory storage medium refers to a storage medium other than a carrier wave. The instructions may also reside, completely or at least partially, within the memory subsystem 1108 and/or within the processing device 1102 during execution thereof by the computer device 1101, the memory subsystem 1108 and the processing device 1102 also constituting computer-readable storage media.

The computer-readable storage medium may also be used to store one or more virtual 3D models and/or a segmented aligner generation module 1150, which may perform one or more of the operations of methods 800-1000 described with reference to FIGS. 8-10. The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1120 includes any means for obtaining a digital representation (e.g., images, surface topography data, etc.) of a patient's teeth (e.g., by scanning physical models of the teeth such as casts, by scanning impressions taken of the teeth, or by directly scanning the intraoral cavity of a patient). Scanner 1120 may receive or generate dental arch data 1121 (which may be data usable to generate a 3D virtual model of a patient's dental arch), and may provide such dental arch data 1121 to computing device 1101. Scanner 1120 may be located at a location remote with respect to other components of the system and can communicate image data and/or information to computing device 1101, for example, via network interface 1124. Fabrication system 1122 fabricates orthodontic aligners 1123 based on a treatment plan, including data set information received from computing device 1101. Fabrication machine 1122 can, for example, be located at a remote location and receive data set information from computing device 1101 via network interface 1124.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
   forming a first segment of a plastic orthodontic aligner for moving a first set of teeth of a patient;
   forming a second segment of the plastic orthodontic aligner; and
   joining the first segment of the plastic orthodontic aligner to the second segment of the plastic orthodontic aligner using a connector configured to minimize force transmission between the first segment and the second segment;
   wherein the connector is configured to be disposed along one or more additional teeth of the patient without exerting a clinically significant force on the one or more additional teeth, wherein the connector spans a gap between the first segment and the second segment, the gap corresponding to the one or more additional teeth that are not to receive the clinically significant force, wherein the connector comprises a flexible material that will perform at least one of flex, move or change shape responsive to applied forces, wherein the connector is configured to isolate first forces applied to the first set of teeth covered by the first segment from separate and distinct second forces applied to a second set of teeth covered by the second segment, and wherein isolation of the first forces from the second forces enables a) the first forces to be applied to the first set of teeth without substantial interference from the second forces applied to the second set of teeth and b) the second forces to be applied to the second set of teeth without substantial interference from the first forces applied to the first set of teeth.

2. The method of claim 1, wherein:
forming the first segment of the plastic orthodontic aligner comprises:
  generating a first mold of a first portion of a dental arch that includes a first model of the first set of teeth; and
  thermoforming or pressure forming the first segment over the first mold; and
forming the second segment of the plastic orthodontic aligner comprises:
  generating a second mold of a second portion of the dental arch that includes a second model of the second set of teeth; and
  thermoforming or pressure forming the second segment over the second mold.

3. The method of claim 1, wherein the forming of the first segment and the forming of the second segment are performed together in a process comprising:
  generating a mold of a dental arch for the patient;
  thermoforming or pressure forming a plastic over the mold to form the plastic orthodontic aligner; and
  cutting the plastic orthodontic aligner to separate the plastic orthodontic aligner into the first segment and the second segment.

4. The method of claim 1, wherein the connector comprises an elastic adhesive that bonds to the first segment at a first end and to the second segment at a second end.

5. The method of claim 1, wherein the connector is to minimize force transmission in a first direction without minimizing force transmission in a second direction.

6. An orthodontic aligner comprising:
a first plastic segment having a first shape that fits over a first portion of a dental arch of a patient, wherein the first plastic segment is configured to apply a force to a first set of teeth in the first portion of the dental arch;
a second plastic segment having a second shape that fits over a second portion of the dental arch of the patient; and
a connector that joins the first plastic segment to the second plastic segment, wherein the connector is to minimize force transmission between the first plastic segment and the second plastic segment, wherein the connector is configured to be disposed along one or more additional teeth of the patient without exerting a clinically significant force on the one or more additional teeth, wherein the connector spans a gap between the first segment and the second segment, the gap corresponding to the one or more additional teeth that are not to receive the clinically significant force, wherein the connector comprises a flexible material that will perform at least one of flex, move or change shape responsive to applied forces, wherein the connector is configured to isolate first forces applied to the first set of teeth covered by the first segment from separate and distinct second forces applied to a second set of teeth covered by the second segment, and wherein isolation of the first forces from the second forces enables a) the first forces to be applied to the first set of teeth without substantial interference from the second forces applied to the second set of teeth and b) the second forces to be applied to the second set of teeth without substantial interference from the first forces applied to the first set of teeth.

7. The orthodontic aligner of claim 6, wherein the connector is to minimize force transmission in a first direction without minimizing force transmission in a second direction.

8. The orthodontic aligner of claim 6, wherein the connector comprises at least one of a semi-rigid thermoset, a semi-rigid thermoplastic, or a semi-rigid metal.

9. The orthodontic aligner of claim 6, wherein the first segment, the second segment and the connector are portions of a single contiguous plastic body.

10. The orthodontic aligner of claim 6, wherein the connector comprises a corrugated configuration that is to flex before applying a third force between the first plastic segment and the second plastic segment.

11. The orthodontic aligner of claim 6, further comprising:
  one or more additional segments, each of the one or more additional segments having an additional shape that fits over an additional portion of the dental arch of the patient; and
  one or more additional connectors that join the one or more additional segments to at least one of the first plastic segment or the second plastic segment.

12. The orthodontic aligner of claim 6, further comprising:
  a retention feature on the first plastic segment configured to receive an elastic band, wherein the elastic band is to apply one of a distal force or a mesial force to the first set of teeth without applying force to the second set of teeth of the patient.

13. The orthodontic aligner of claim 6, wherein the first plastic segment comprises a first feature configured to retain a first end of the connector and the second plastic segment comprises a second feature configured to retain a second end of the connector.

14. A non-transitory computer readable storage medium having instructions that, when executed to by a processing device, cause the processing device to perform operations comprising:
  causing, by the processing device, formation of a first segment of a plastic orthodontic aligner for moving a first set of teeth of a patient and a second segment of the plastic orthodontic aligner, the causing of the formation comprising:
    receiving, by the processing device, a digital three-dimensional model of a dental arch of the patient;
    sending, by the processing device, first instructions to a rapid prototyping machine to cause the rapid prototyping machine to produce a physical mold of the dental arch based on the digital three-dimensional model;
    after the physical mold is formed, sending second instructions to a thermoforming or pressure forming machine to cause the thermoforming or pressure forming machine to create the plastic orthodontic aligner based on thermoforming or pressure forming a plastic sheet to the physical mold; and sending, by the processing device, third instructions to a cutting machine to cause the cutting machine to cut the plastic orthodontic aligner into at least the first segment and the second segment; and causing, by the processing device, joining of the first segment of the plastic orthodontic aligner to the second segment of the plastic orthodontic aligner using a connector configured to minimize force transmission between the first segment and the second segment, the causing of the joining comprising:

sending fourth instructions to attach the connector between the first segment and the second segment, wherein the connector is configured to be disposed along one or more additional teeth of the patient without exerting a clinically significant force on the one or more additional teeth, wherein the connector spans a gap between the first segment and the second segment, the gap corresponding to the one or more additional teeth that are not to receive the clinically significant force, wherein the connector comprises a flexible material that will perform at least one of flex, move or change shape responsive to applied forces, wherein the connector is configured to isolate first forces applied to the first set of teeth covered by the first segment from separate and distinct second forces applied to a second set of teeth covered by the second segment, and wherein isolation of the first forces from the second forces enables a) the first forces to be applied to the first set of teeth without substantial interference from the second forces applied to the second set of teeth and b) the second forces to be applied to the second set of teeth without substantial interference from the first forces applied to the first set of teeth.

15. The non-transitory computer readable storage medium of claim 14, wherein the digital three-dimensional model comprises a first feature that causes the first segment to include a first retaining feature configured to retain a first end of the connector and a second feature that causes the second segment to include a second retaining feature configured to retain a second end of the connector.

16. The non-transitory computer readable storage medium of claim 14, the operations further comprising:

sending fifth instructions to a machine to cause the machine to form a retention feature on the first segment configured to receive an elastic band, wherein the elastic band is to apply a distal force to the first set of teeth without applying force to the second set of teeth of the patient.

* * * * *